(12) United States Patent
Engelhard

(10) Patent No.: US 7,582,433 B2
(45) Date of Patent: Sep. 1, 2009

(54) DEVICES FOR GENERATING DETECTABLE POLYMERS

(75) Inventor: Eric K. Engelhard, Davis, CA (US)

(73) Assignee: Fair Isaac Corporation, Minneapolis, MN (US)

( * ) Notice: Subject to any disclaimer, the term of this patent is extended or adjusted under 35 U.S.C. 154(b) by 0 days.

(21) Appl. No.: 11/548,980

(22) Filed: Oct. 12, 2006

(65) Prior Publication Data

US 2008/0090228 A1 Apr. 17, 2008

(51) Int. Cl.
*C12Q 1/68* (2006.01)
*C12P 19/34* (2006.01)
*C12M 1/00* (2006.01)

(52) U.S. Cl. .................. 435/6; 435/91.2; 435/287.2

(58) Field of Classification Search .................. None
See application file for complete search history.

(56) References Cited

U.S. PATENT DOCUMENTS 6,875,619 B2 * 4/2005 Blackburn .................. 436/514
2004/0043479 A1 * 3/2004 Briscoe et al. ........... 435/288.5

FOREIGN PATENT DOCUMENTS

WO WO 02/01180 A2 * 1/2002

OTHER PUBLICATIONS

Ko et al., "Rapid detection of infectious adenoviruses by mRNA real-time RT-PCR," J.Virol.methods, Aug. 2005, vol. 127, pp. 148-153.*
Cepheid, "SmartSystem: SmartCycler," product brochure, Jun. 2005, pp. 1-6.*
Watanabe et al., "Detection of adenovirus DNA in clinical samples by SYBR Green real-time polymerase chain reaction assay," Pediatrics Intern., Jun. 2005, vol. 47, pp. 286-291.*
Applied Biosystems Press Release, "PE BioSystems Announces Launch of ABI Prism 7900HT Sequence Detection System," Nov. 20, 2000, pp. 1-2 (http://www.appliedbiosystems.com/press_releases/7900launch/).*
Payungpron, et al., "Single step multiplex real-time RT-PCR for H5N1 Influencza A virus detection," J. Virol. Methods, Jan. 2006, vol. 131, pp. 143.*
Kraft et al., "Evaluation of PCR Testing of Ethanol-Fixed Nasal Swab Specimens as an Augmented Surveillance Strategy for Influenza Virus and Adenovirus Identification," J. Clin.Microbiol., Apr. 2005, vol. 43, No. 4, pp. 1768-1775.*
Wu et al., "Development of Taqman RT-nested PCR system for clinical SARS-CoV detection," J. Virol Methods, 2004, vol. 119, pp. 17-23.*
Leamon et al., "A massively parallel PicoTiterPlate based Platform for discrete picoliter-scale polymerase chain reactions," Electrophoresis, 2003, vol. 24, pp. 3769-3777.*
Wittwer et al., "The LightCycler: A Microvolume Multisample Fluorimeter with Rapid Temperature Control," Biotechniques, 1997, vol. 22, pp. 176-181.*
Richards et al., "A SYBR green, real-time RT-PCR method to detect and quantitate Norwalk virus in stools," J. Virol. Methods, 2004, vol. 116, pp. 63-70.*
Dewhurst-Maridor et al., "Development of a quantitative TaqMan RT-PCR for respiratory syncytial virus," J. Virol. Methods, 2004, vol. 120, pp. 41-49.*
GenBank Accession No. AB067658, referenced as 15076670, dated Aug. 2, 2001, 2 pages.
GenBank Accession No. AB243009, referenced as 83017238, dated Dec. 2, 2005, 3 pages.
GenBank Accession No. AF053085, referenced as 3582745, dated Sep. 12, 1998, 3 pages.
GenBank Accession No. AF065065, referenced as 11968173, dated Dec. 22, 2000, 4 pages.
GenBank Accession No. AF065066, referenced as 11641372, dated Dec. 14, 2000, 4 pages.
GenBank Accession No. AF321311, referenced as 16930159, dated May 22, 2002, 2 pages.
GenBank Accession No. AY337253, referenced as 37702194, dated Apr. 8, 2004, 2 pages.
GenBank Accession No. AY337258, referenced as 37702204, dated Apr. 8, 2004, 2 pages.
GenBank Accession No. AY495969, referenced as 40786870, dated Jan. 14, 2004, 17 pages.
GenBank Accession No. AY594255, referenced as 51173294, dated May 10, 2006, 22 pages.
GenBank Accession No. AY594256, referenced as 55847711, dated May 10, 2006, 23 pages.
GenBank Accession No. AY599834, referenced as 57115749, dated May 10, 2006, 21 pages.
GenBank Accession No. AY601634, referenced as 57115983, dated May 10, 2006, 23 pages.
GenBank Accession No. DQ099432, referenced as 93302091, dated Apr. 25, 2006, 22 pages.
GenBank Accession No. DQ115429, referenced as 69139752, dated Jul. 20, 2006, 2 pages.
GenBank Accession No. DQ177310, referenced as 74229858, dated Sep. 12, 2005, 2 pages.
GenBank Accession No. U75955, referenced as 2511449, dated Aug. 3, 2001, 2 pages.
GenBank Accession No. U77390, referenced as 1710306, dated Aug. 3, 2001, 2 pages.
GenBank Accession No. U77391, referenced as 1710308, dated Aug. 3, 2001, 2 pages.
GenBank Accession No. X76549, referenced as 3641840, dated Apr. 18, 2005, 3 pages.
GenBank Accession No. X76552, referenced as 434911, dated Apr. 18, 2005, 2 pages.
Beaucage and Caruthers, "Deoxynucleoside Phosphoramidites—A New Class of Key Intermediates for Deoxypolynucleotide Synthesis," *Tetrahedron Lett.*, 1981, 22:1859-1862.

* cited by examiner

*Primary Examiner*—Kenneth R. Horlick
*Assistant Examiner*—Molly E Baughman
(74) *Attorney, Agent, or Firm*—Fish & Richardson P.C.

(57) ABSTRACT

This document provides systems, devices, and methods involved in generating detectable polymers. For example, diagnostic systems, diagnostic devices, primer systems, and collections of primer systems are provided.

17 Claims, 1 Drawing Sheet

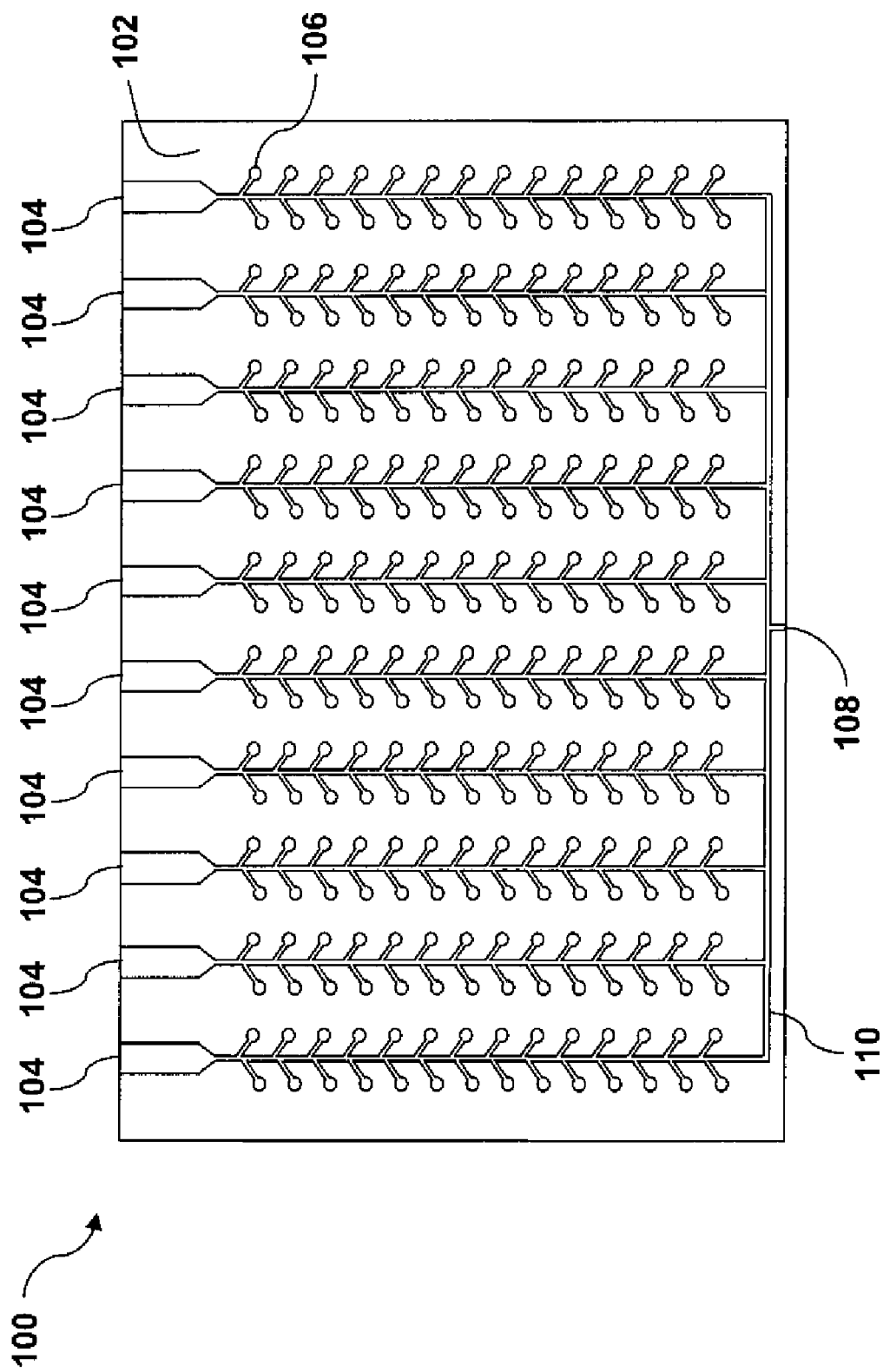

SEQUENCE LISTING

<160> NUMBER OF SEQ ID NOS: 5

<210> SEQ ID NO 1
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 1
caacagtact ggaaatatgg gagtt                                         25

<210> SEQ ID NO 2
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 2
agaatcaagc aaaagctgat atgac                                         25

<210> SEQ ID NO 3
<211> LENGTH: 25
<212> TYPE: DNA
<213> ORGANISM: Artificial Sequence -continued

```
<220> FEATURE:
<223> OTHER INFORMATION: Synthetically generated oligonucleotide

<400> SEQUENCE: 3
attgatatgg aatttttcga tggta                                            25

<210> SEQ ID NO 4
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 4
aactcccata tttccagtac tgttg                                            25

<210> SEQ ID NO 5
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 5
tattgatatg gaatttttcg atggt                                            25
```

DEVICES FOR GENERATING DETECTABLE POLYMERS

BACKGROUND

1. Technical Field

This document relates to systems, devices, and methods involved in generating detectable polymers.

2. Background Information

Many different types of devices exist for generating polymers such as labeled deoxyribonucleic acids. For example, tubes, tube retainer trays, microtiter plates, microfluidic cards, and glass slides containing arrays have been fabricated to allow a user to generate polymers. The HT7900 Micro Fluidic Card™ is an example of a microfluidic card designed to allow a user to generate polymers. In this case, the microfluidic card functions as a structured array of reaction chambers and contains input ports for inserting samples into the card. The HT7900 Micro Fluidic Card™ is available from Applied Biosystems Group (Foster City, Calif.).

In addition, many different techniques have been developed to detect a generated polymer. For example, machines designed to read fluorescent signals from each well of a microtiter plate have been developed. The FLx800™ reader is an example of an absorbance and fluorescence instrument for measuring samples in various microplate arrangements. The reader can used in numerous fluorescence and absorbance applications in research and routine investigations. Its fluorescence filters are arranged in filter wheels. The reader can handle 6, 48, 96, and 384 well plates and can detect wavelengths in the fluorescence spectral range. Gen5™ data collection and analysis software can be used for data capture, and standard reads and data can be downloaded into Excel for further analysis. Dual optical channels can allow for measurements from above or below the plate. Light to and from the samples can be focused by a lens. The FLx800™ reader is available from BioTek Instruments, Inc. (Winooski, Vt.).

SUMMARY

This document relates to systems, devices, and methods involved in generating detectable polymers. For example, this document provides diagnostic systems, diagnostic devices, primer systems, and collections of primer systems. A diagnostic system can include a diagnostic device containing a collection of primer systems. This document also provides methods for making diagnostic systems, diagnostic devices, primer systems, and collections of primer systems. For example, this document provides methods for making a diagnostic device containing a collection of primer systems. The systems, devices, and methods provided herein can be used to generate detectable polymers such as amplified deoxyribonucleic acid molecules. In addition, the systems, devices, and methods provided herein can be used to detect adenoviruses within samples. Detecting adenoviruses can help clinicians provide important prognostic information to patients.

The description provided herein is based, in part, on the discovery of effective primer systems for generating detectable polymers. For example, a diagnostic device provided herein can contain primer systems effective to detect adenoviruses within samples. Such a diagnostic device can be used to aid clinicians in assessing a patient's prognosis. The description provided herein also is based, in part, on the discovery of primer systems having the ability to not only amplify particular nucleic acid sequences from different adenoviruses, but also to not amplify nucleic acid sequences from non-adenovirus sources such as a human's genome. In addition, the description provided herein is based, in part, on the discovery of primer systems that can be used simultaneously with a collection of primer pairs under the same amplification reaction conditions to amplify different target nucleic acids if present in the sample being tested.

In general, one aspect of this document features a device comprising, or consisting essentially of, a housing having a plurality of locations, wherein each of the locations contains a primer system, wherein the primers of each primer system are between 18 and 28 nucleotides in length and have a theoretical melting temperature between 58° C. and 62° C., wherein the device comprises at least one primer system capable of producing an amplification product diagnostic for an adenovirus, and wherein each amplification product, when produced, is between 100 and 400 nucleotides in length. Each of the locations can be a chamber. Each of the locations can be a well. The primers of each primer system can be between 23 and 27 nucleotides in length. The primers of each primer system can have a theoretical melting temperature between 59° C. and 61° C. The housing can comprise additional locations, wherein each of the additional locations contains a primer pair. At least one of the additional locations can comprise a primer pair capable of producing an amplification product from human nucleic acid. Each of the locations can comprise an intercalating dye, and wherein each amplification product, when produced, can be labeled with the intercalating dye. The intercalating dye can be a green fluorescent dye. The intercalating dye can be SYBR Green, LC Green, or SYTO9. Each amplification product, when produced, can be between 100 and 300 nucleotides in length.

In another aspect, this document features method for detecting an adenovirus within a sample. The method comprises, or consists essentially of, (a) performing a nucleic acid amplification reaction using the sample as a source of template and a diagnostic device, wherein the device comprises a housing having a plurality of locations, wherein each of the locations contains a primer system, wherein the primers of each primer system are between 18 and 28 nucleotides in length and have a theoretical melting temperature between 58° C. and 62° C., wherein the device is capable of producing an amplification product diagnostic for an adenovirus, and wherein each amplification product, when produced, is between 100 and 400 nucleotides in length, and (b) determining which locations of the device contain a primer system that resulted in the formation of amplification product, thereby detecting an adenovirus. The sample can be a sample obtained from a human. The nucleic acid amplification reaction can comprise at least 10 cycles. The nucleic acid amplification reaction can comprise at least 20 cycles. The nucleic acid amplification reaction can comprise a denaturing step at about 94° C. or about 95° C. The nucleic acid amplification reaction can comprise an annealing step at about 60° C. The nucleic acid amplification reaction can comprise an extension step at about 72° C. The sample can be a mucus sample. The sample can be a sample obtained from the human using a swab. The sample can be a sample processed to obtain viral nucleic acid. Each of the locations can comprise an intercalating dye, wherein each amplification product, when produced, is labeled with the intercalating dye, and wherein determining which locations of the device contain a primer system that resulted in the formation of amplification product is based on a signal from the dye. The amplification reaction can be performed in a thermal cycler device configured to receive the diagnostic device. The determining step (b) can be performed in using a dye reader device configured to receive the diagnostic device. The amplification reaction and the determining step (b) can be performed in a machine configured to receive the diagnostic device, the machine comprising a thermal cycler device and a dye reader device. The machine can be capable of providing output indicating the presence of the adenovirus. The machine can be capable of providing output indicating the primer system that detected the presence of the adenovirus. The output can be a paper printout or a computer readable file.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1 is a top view of a microfluidic card.

DETAILED DESCRIPTION

This document provides systems, devices, and methods involved in generating detectable polymers. For example, this document provides diagnostic systems, diagnostic devices, primer systems, and collections of primer systems. A diagnostic system can include a diagnostic device containing primer systems.

In general, a diagnostic device provided herein can include a housing having a plurality of locations. The housing can be any shape and size and can be made from any type of material including, without limitation, plastic, glass, silicone, or metal. For example, a housing provided herein can be rectangular, square, circular, or oval in shape, and can have a length, width, or diameter between five cm and 50 cm (e.g., between ten cm and 40 cm, between ten cm and 30 cm, or between ten cm and 25 cm). The depth or height of a housing provided herein can be between 0.2 cm and 2 cm (e.g., between 0.2 and 1 cm, between 0.3 and 1 cm, or between 0.5 and 1 cm). Each location of a housing can be configured to allow an amplification reaction to occur without primer system contamination from other locations. The locations of a housing provided herein can be any shape or size. For example, the locations of a housing provided herein can be in the configuration of a well or chamber with, for example, the ability to hold a volume between 1 µL and 100 µL (e.g., between 1 µL and 20 µL, between 1 µL and 10 µL, between 1 µL and 5 µL, between 10 µL and 50 µL, or between 15 µL and 25 µL). Such a volume can be 1.5 µL, 10 µL, 20 µL, or 30 µL. In some cases, a housing can be a 96-well plate with each location being a well of the 96-well plate. A diagnostic device can be in the form of a microfluidic card. Such a card can have a series of locations and channels. The channels can provide fluid communication between a sample inlet port and one or more locations. For example, a housing can be a mircofluidic card having one or more sample inlet ports in fluid communication with one or more locations via one or more channels. In some cases, such a housing can include one or more outlet ports for providing an outlet for added solutions or for providing an outlet for air so that fluid can flow through the channels. In one embodiment, a diagnostic device provided herein can be in the form of a microfluidic card with eight sample inlet ports each connected through channels (e.g., microcapillaries) to 48 locations (e.g., reaction chambers). Another example of a microfluidic card design is depicted in FIG. 1.

With reference to FIG. 1, microfluidic card 100 can have housing 102 defining a plurality of locations 106. While 280 separate locations are shown in this example, a housing provided herein can define any number of locations (e.g., 10, 25, 48, 96, 384, 1536, or more locations). Each location 106 can be in fluid communication with a sample inlet port 104 and an outlet port 108 via channel 110. Any number of channels can be defined by housing 102. For example, a housing provided herein can define one continuous, interconnected channel or can contain multiple separate channels.

A diagnostic device provided herein can contain a collection of primer systems and primer pairs. For example, each primer system or primer pair of a collection can be located at a different location defined by a housing so as to isolate each primer system or primer pair from other primer systems or primer pairs of a collection. For example, each primer system or primer pair of a collection can be housed within a separate location (e.g., a separate well of a plastic microtiter plate or a separate chamber of a microfluidic card). In some cases, each primer system or primer pair of a collection, or a subset of primer systems or primer pair of a collection, can be housed together. For example, one primer system provided herein and one primer pair of a collection of 50 primer systems and primer pairs can be housed within a single well of a plastic microtiter plate with the remaining 48 primer systems and primer pairs being housed within separate wells. In some cases, a system or diagnostic device provided herein can contain at least one primer system set forth in Table 1 (e.g., at least two primer systems set forth in Table 1). In addition to containing any one or more of the primer systems set forth in Table 1 in any combination, a diagnostic device can contain primer systems not listed in Table 1. For example, a diagnostic device can contain a primer system similar to primer system number 1 with the exception that each nucleic acid primer is two nucleotides shorter than those of primer system number 1. In some cases, a diagnostic device can contain a primer pair designed to amplify host nucleic acid (e.g., human genomic nucleic acid or mRNA).

TABLE 1

Optimal primer systems for adenoviruses.

| Primer System No. | Primer Sequence | SEQ ID NO: | Length | Tm | Hits* |
|---|---|---|---|---|---|
| 1 | CAACAGTACTGGAAATATGGGAGTT | 1 | 25 | 59.7 | 89 |
|  | AGAATCAAGCAAAAGCTGATATGAC | 2 | 25 | 60.2 |  |

TABLE 1-continued

Optimal primer systems for adenoviruses.

| Primer System No. | Primer Sequence | SEQ ID NO: | Length | Tm | Hits* |
|---|---|---|---|---|---|
| 2 | ATTGATATGGAATTTTTCGATGGTA | 3 | 25 | 59.8 | 85 |
|   | AACTCCCATATTTCCAGTACTGTTG | 4 | 25 | 59.7 |   |
| 3 | TATTGATATGGAATTTTTCGATGGT | 5 | 25 | 59.8 | 85 |
|   | AACTCCCATATTTCCAGTACTGTTG | 4 | 25 | 59.7 |   |

*total number of different gi numbers that is available in GenBank with nucleic acid sequences aligning with each primer of the indicated primer system.

The term "primer system" as used herein refers to a combination of two nucleic acid primers having the ability to amplify nucleic acid provided that the sequence of each nucleic acid primer is from 15 to 50 nucleotides in length and is such that it aligns without a mismatch to a sequence, or its complement, set forth in a GenBank gi number listed in Table 2. For example, each primer of a primer system provided herein can be from 15 to 45 nucleotides the length. In some cases, each primer of a primer system provided herein can range from 20 to 40 nucleotides (e.g., from 20 to 35 nucleotides, from 20 to 30 nucleotides, or from 21 to 28 nucleotides). The primer systems provided herein can be selected such that the length of amplified target nucleic acid, if present within an amplification reaction, would be between 100 and 400 nucleotides (e.g., between 150 and 350 nucleotides, between 175 and 325 nucleotides, or between 200 and 300 nucleotides). The theoretical melting temperature of each primer of a primer system provided herein can be between 58° C. and 62° C. (e.g., between 59° C. and 61° C.). A primer's theoretical melting temperature is calculated as follows:

$$Tm = 81.5 + 16.6(\log 10([Na+])) + 0.41*(\% GC) - 600/\text{length}$$

where [Na+] is 0.005 M. Each primer system provided herein can be used to amplify nucleic acid present in an adenovirus.

TABLE 2

Representative gi numbers for each primer system.

| Primer System No. | gi number |
|---|---|
| 1 | 3641840 (SEQ ID NO:6); 15076670 (SEQ ID NO:7); 1710306 (SEQ ID NO:8); 3582745 (SEQ ID NO:9); 37702194 (SEQ ID NO:10); 11641372 (SEQ ID NO:11); 93302091 (SEQ ID NO:12); 11968173 (SEQ ID NO:13); 57115749 (SEQ ID NO:14); 83017238 (SEQ ID NO:15); 40786870 (SEQ ID NO:16); 51173294 (SEQ ID NO:17); 55847711 (SEQ ID NO:18); 57115983 (SEQ ID NO:19); 16930159 (SEQ ID NO:20); 37702204 (SEQ ID NO:21); 434911 (SEQ ID NO:22); 74229858 (SEQ ID NO:23); and 2511449 (SEQ ID NO:24) |
| 2, 3 | 3641840 (SEQ ID NO:6); 15076670 (SEQ ID NO:7); 1710308 (SEQ ID NO:25); 3582745 (SEQ ID NO:9); 37702194 (SEQ ID NO:10); 11641372 (SEQ ID NO:11); 93302091 (SEQ ID NO:12); 57115749 (SEQ ID NO:14); 83017238 (SEQ ID NO:15); 40786870 (SEQ ID NO:16); 55847711 (SEQ ID NO:18); 57115983 (SEQ ID NO:19); 16930159 (SEQ ID NO:20); 434911 (SEQ ID NO:22); 74229858 (SEQ ID NO:23); and 69139752 (SEQ ID NO:26) |

The primer systems provided herein can share unifying advantageous features. For example, each primer system provided herein can amplify nucleic acid from adenoviruses. In addition, primer systems provided herein can be selected such that the length of amplified viral nucleic acid would be between 100 and 400 nucleotides. Moreover, the theoretical melting temperature of the primer systems provided herein can be uniformly between 58° C. and 62° C., and the length of each primer of the primer systems provided herein can range from 15 to 50 nucleotides (e.g., from 21 to 28 nucleotides). These unifying characteristics can contribute to the effective detection of nucleic acid from adenoviruses present within samples.

The primer systems listed in Table 1 can be used effectively to detect a large group of different adenoviruses. For example, primer system number 1 can have the ability to detect adenovirus nucleic acid sequences associated with 89 different GenBank gi numbers.

Any method can be used to make the primers of a primer system provided herein. For example, chemical synthesis techniques such as those described elsewhere (Beaucage and Caruthers, *Tetrahedron Lett.*, 22:1859-62 (1981)) can be used. In addition, nucleic acid primers can be obtained from commercial vendors such as MWG Biotech, Invitrogen, and Operon.

Any method can be use to make a system or diagnostic device provided herein. For example, a diagnostic device provided herein can be made as follows. A 384-well master plate containing 125 μL of one or more primer systems in dioinized water at a working concentration of 100 nmole/1 μL of each primer can be constructed. The master plate can be used as a template source, and 1 μL of each master plate well can be transferred to corresponding wells on a 384-well microfluidic card. Spotted reagents can be allowed to dry at room temperature before the final plastic laminate layer of the microfluidic card is attached.

The primer systems provided herein can be used separately or in combinations with other primer systems provided in Table 1 or other primer pairs. When making a combination, any two or more primer pairs or primer systems provided herein can be arranged into any combination.

The diagnostic devices and primer systems provided herein can be used to detect adenoviruses present within samples. For example, a sample can be obtained from a human (or other animal such as a bird) and used in an amplification reaction to determine whether or not an adenovirus' nucleic acid is present in the sample. Any type of sample can be used including, without limitation, a biopsy (e.g., punch biopsy, aspiration biopsy, excision biopsy, needle biopsy, or shave biopsy), a tissue section, lymph fluid, mucus, blood, serum, and saliva samples. A sample can be obtained from a human or any other animal suspected to contain an adenovirus (e.g., birds, pigs, and horses). In some cases, a sample can be obtained from a mammal (e.g., a human) using a swab (e.g., an OmniSwab; Whatman). The presence of an amplification product following an amplification reaction using, for example, a human's mucus sample and a primer system provided herein can indicate that that sample contains an adenovirus. In such a case, the human can be diagnosed as being infected with an adenovirus.

Some sample types can be pre-processed to enhance sample quality. For example, a mucus sample can be treated with a mucolytic agent to liquefy mucus within a mucus sample. Samples can be processed to concentrate the nucleic acid and render it in a form to facilitate successful PCR reactions. This includes, but is not limited to, common methods to disrupt bilipid membranes, such as the use of detergents, digestion of protein complexes, such as the use of proteinase K, and reduction of polymerase inhibitors through the use of selective affinity columns. Commercial kits for purification of DNA, RNA, or total nucleic acid are readily available from, for example, Qiagen and Roche. In some cases, a sample can be processed using a Qiagen QIAmp Viral RNA Mini Kit.

Any type of amplification reaction can be used in conjunction with the primer systems set forth in Table 1 to detect adenoviruses. For example, common PCR reactions designed to amplify nucleic acid from DNA or RNA can be used. Detection of RNA viruses can be accomplished by synthesizing cDNA from RNA sequence templates. cDNA synthesis can be accomplished using standard methods using, for example, RNA-dependant DNA polymerases, such as reverse transcriptase. Such reactions can be primed with random oligonucleotide sequences, such as random hexamers and octamers, or by sequence specific oligonucleotide primers, including the same primers used for the PCR reaction. The cDNA synthesis can be performed in a separate reaction vessel from the subsequent PCR reaction (commonly referred to as two-step rtPCR) or in the same reaction vessel as the PCR reaction (commonly referred to as single-step rtPCR).

Purified DNA and cDNA samples can be pooled and added to a PCR master mix containing water, salt buffers, magnesium ions, nucleotide monomers (dATP, dCTP, dGTP and dTTP), native or engineered *Thermus aquaticus* DNA-dependant DNA polymerase, and an intercalating dye, such as Sybr Green or LC Green. The master mix and sample can then be added to a single loading port of a microfluidic card and dispersed to all the reaction wells using centrifugation. The cards can then be scored to isolate and seal each reaction chamber prior to thermocycling. The cards can be individually thermocycled using commodity block thermocyclers or many cards thermocycled simultaneously using air- or water-based thermocyclers such as the BioOven or the H2OBIT, respectively.

Positive PCR amplification reactions can be detected during thermocycling for quantitative or qualitative analysis (real time PCR) or after completion of thermocycling (qualitative end-point PCR). Signals can be detected through fluorescence-channel emission of substrate bound intercalating dyes using commodity real-time PCR capable PCR platforms or by end-point reads using microplate scanner platforms. Both types of platforms can be used for melting-point analysis for validation of positive signals.

OTHER EMBODIMENTS

It is to be understood that while the invention has been described in conjunction with the detailed description thereof the foregoing description is intended to illustrate and not limit the scope of the invention, which is defined by the scope of the appended claims. Other aspects, advantages, and modifications are within the scope of the following claims.

What is claimed is:

1. A device comprising a housing having a plurality of locations, wherein at least one of said locations comprises any one of Primer Systems 1, 2, or 3 of Table 1.

2. The device of claim 1, wherein each of said locations is a chamber.

3. The device of claim 1, wherein each of said locations is a well.

4. The device of claim 1, wherein at least one of said locations comprises a different primer pair.

5. The device of claim 4, wherein said different primer pair capable of producing an amplification product from human nucleic acid.

6. The device of claim 1, wherein each of said locations comprises an intercalating dye.

7. The device of claim 6, wherein said intercalating dye is a green fluorescent dye.

8. The device of claim 6, wherein said intercalating dye is SYBR Green, LC Green, or SYTO9.

9. A method for detecting an adenovirus within a sample, wherein said method comprises:
    (a) performing a nucleic acid amplification reaction using said sample as a source of template and a diagnostic device, wherein said device comprises a housing having a plurality of locations, wherein at least one of said locations contains any one of Primer Systems 1, 2, or 3 of Table 1, and
    (b) determining whether or not the location containing said primer system comprises said amplification product, thereby detecting an adenovirus.

10. The method of claim 9, wherein said sample is a mucus sample obtained from a human.

11. The method of claim 9, wherein each of said locations comprises an intercalating dye, wherein each amplification product, when produced, is labeled with said intercalating dye, and wherein said determining step (b) comprises assessing a signal from said dye.

12. The method of claim 9, wherein said amplification reaction is performed in a thermal cycler device configured to receive said diagnostic device.

13. The method of claim 9, wherein said determining step (b) is performed using a dye reader device configured to receive said diagnostic device.

14. The method of claim 9, wherein said amplification reaction and said determining step (b) are performed in a machine configured to receive said diagnostic device, said machine comprising a thermal cycler device and a dye reader device.

15. The method of claim 14, wherein said machine is capable of providing output indicating the presence of said adenovirus.

16. The method of claim 14, wherein said machine is capable of providing output identifying indicating the primer system that detected the presence of said adenovirus.

17. The method of claim 16, wherein said output is a paper printout or a computer readable file.

* * * * *

UNITED STATES PATENT AND TRADEMARK OFFICE
CERTIFICATE OF CORRECTION

PATENT NO. : 7,582,433 B2
APPLICATION NO. : 11/548980
DATED : September 1, 2009
INVENTOR(S) : Eric K. Engelhard It is certified that error appears in the above-identified patent and that said Letters Patent is hereby corrected as shown below:

Title Page, under References Cited, Other Publications, Payungpron et al. reference, please delete "Influencza" and insert --Influenza-- therefor;

Column 10, line 54 (Claim 16), after "output" please delete "identifying".

Signed and Sealed this

Tenth Day of November, 2009

David J. Kappos
*Director of the United States Patent and Trademark Office*